(12) United States Patent
Keirsbilck

(10) Patent No.: US 6,589,171 B2
(45) Date of Patent: Jul. 8, 2003

(54) SENSOR GLOVE FOR PHYSIOLOGICAL PARAMETER MEASUREMENT

(75) Inventor: Richard S. Keirsbilck, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/892,824

(22) Filed: Jun. 27, 2001

(65) Prior Publication Data

US 2003/0009087 A1 Jan. 9, 2003

(51) Int. Cl.⁷ .................................................. A61B 5/00
(52) U.S. Cl. ................. 600/300; 600/346; 600/372; 600/549; 600/323; 600/384
(58) Field of Search ............... 600/300–301, 600/306, 346, 384, 372, 382, 388, 549, 323–344, 310, 322

(56) References Cited

U.S. PATENT DOCUMENTS

| | | | |
|---|---|---|---|
| 3,983,753 A | 10/1976 | Greenleaf et al. | |
| 4,055,166 A | 10/1977 | Simpson et al. | |
| 4,414,984 A | 11/1983 | Zarudiansky | |
| 4,509,531 A | 4/1985 | Ward | |
| 4,510,939 A * | 4/1985 | Brenman et al. | 128/639 |
| 5,362,966 A | 11/1994 | Rosenthal et al. | |
| 5,374,283 A * | 12/1994 | Flick | 607/46 |
| 5,964,701 A | 10/1999 | Asada et al. | |
| 6,067,468 A | 5/2000 | Korenman et al. | |
| 6,080,690 A * | 6/2000 | Lebby et al. | 442/209 |
| 6,117,075 A | 9/2000 | Barnea | |
| 6,128,004 A * | 10/2000 | McDowall et al. | 345/158 |
| 6,248,064 B1 * | 6/2001 | Gopinathan et al. | 600/300 |
| 6,394,963 B1 * | 5/2002 | Blazey et al. | 600/549 |

* cited by examiner

Primary Examiner—Teresa Walberg
Assistant Examiner—Shawntina T. Fuqua
(74) Attorney, Agent, or Firm—William F. Noval

(57) ABSTRACT

Apparatus for temporarily attaching a sensor of a physiological parameter to an extremity of a person. The apparatus includes a fabric structure configured to be positioned on an extremity of a person, the fabric structure advantageously formed of loops of yarn-like material which exhibit porosity and controlled elasticity; and sensor(s) of physiological parameters mounted on the fabric structure such that when the structure is positioned on the extremity of a person, the sensors sense physiological parameters of the person.

14 Claims, 6 Drawing Sheets

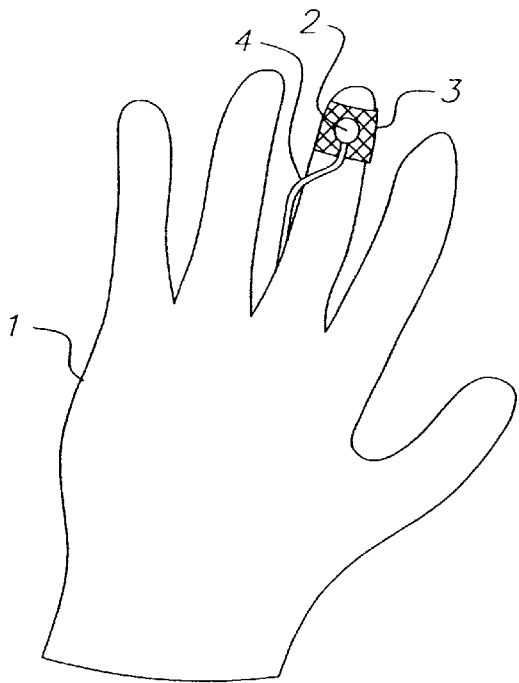
FIG. 1
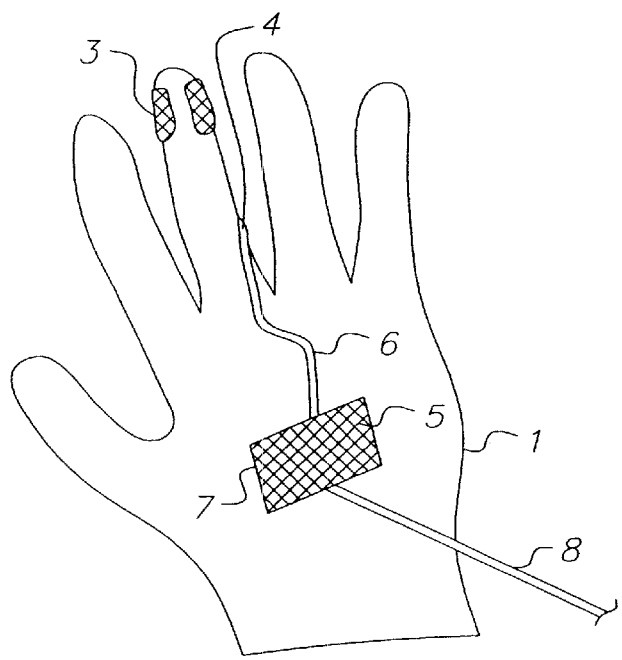
FIG. 2
SESSION LOG ENTRY
| | |
|---|---|
| 353 | Checked me out in mirror. |
| 375 | Took off glasses & moved right to head. |
| 380 | Pulled left hand into lap. |
| 450 | Readjusted in chair. |
| 500 | Right hand still held next to |
| 1 | forehead, left hand still in lap. |
FIG. 3a

SENSOR GLOVE FOR PHYSIOLOGICAL PARAMETER MEASUREMENT

CROSS REFERENCE TO RELATED APPLICATIONS

Reference is made to U.S. patent application Ser. No. 09/597,610, filed Jun. 20, 2000 now U.S. Pat. No. 6,394,963.

FIELD OF THE INVENTION

This invention relates in general to the measurement of physiological parameters of a subject and more particularly to methods and apparatus used to temporarily attach sensors to the hand/fingers for the purpose of measuring various physiological parameters, such as temperature, galvanic skin response, heart pulse rate, perspiration, etc.

BACKGROUND OF THE INVENTION

There are many clinical biofeedback and physiology measurement and monitoring systems in use. These systems are used by professional clinicians, researchers, and others to monitor a subject's physiologic changes, and accordingly use different protocols for various purposes. For example, U.S. Pat. No. 6,117,075 Barnea discloses a method of measuring the depth of anesthesia by detecting the suppression of peripheral skin temperature variability. The peripheral skin temperature is measured by temperature probes on index fingers or thumbs of a patient.

Known apparatus for the purpose of attaching the sensors to the hand or finger to accomplish these measurements include bands, rings, and tensioned clips. Methods include adhesive tape, and self-adhering sensors.

Thus, U.S. Pat. No. 3,983,753, issued Oct. 5, 1976, inventors Greenleaf et al. and U.S. Pat. No. 4,509,531, issued Apr. 9, 1985, inventor Ward, discloses the use of wristbands to attach temperature sensors to a subject. U.S. Pat. No. 5,964,701, issued Oct. 12, 1999, inventors Asada et al. and U.S. Pat. No. 6,067,468, issued May 23, 2000, inventors Korenman et al., discloses the use of finger rings or bands to attach sensors to a subject. The latter patent also discloses the use of wristbands for sensor attachment. U.S. Pat. No. 5,362,966, issued Nov. 8, 1994, inventors Rosenthal et al. discloses a temperature-sensing thermistor-type ring worn around the base of the finger for sensing peripheral skin temperature. A light shield glove is also disclosed but is not used to support the temperature sensor. U.S. Pat. No. 4,055,166, issued Oct. 25, 1977, inventors Simpson et al., discloses a brassiere which includes a number of skin temperature sensors. Although "other garments" besides brassieres are mentioned, there is no specific reference to a glove-like apparatus consisting of a fabric with advantageous features. U.S. Pat. No. 4,414,984, issued Nov. 15, 1983, inventor Zarudiansky, discloses apparatus for recording tactile sensations including a sensing or "receptor" glove used to effect a tactile exploration of an object whose "feel" is to be recorded. The glove includes a mosaic of pressure and temperature sensors preferably formed by localized diffusions of electrically conductive material into a sheet of a flexible insulating material, of the synthetic rubber type. This teaches away from the present invention, in regards to both: using currently-available e.g., inexpensive sensors, and, having a non-insulative function.

The means described above for attaching sensors to an individual all variously exhibit one or more of the following shortcomings:

restriction of blood flow variability in placement variability in contact pressure variability in sensor-to-skin bond/falling off thermal-mass dampening of short-term variation (that which is sought to be measured)

susceptibility to contact with other thermal masses inhibition of normal function of heat radiation and moisture evaporation quality and longevity of the strain relief of the connecting wires comfort of the subject over time apprehension by younger subjects, due to the clinical "look" of the attaching apparatus

SUMMARY OF THE INVENTION

According to the present invention, there is provided a solution to the problems and fulfillment of all the needs set forth above.

According to a feature of the present invention, there is provided an apparatus for temporarily attaching a sensor of a physiological parameter to an extremity of a person comprising:

a fabric structure configured to be positioned on an extremity of a person, said fabric structure formed of loops of yarn like material which exhibit porosity and elasticity; and a sensor of a physiological parameter mounted on said fabric structure such that when said structure is positioned on the extremity of a person, said sensor senses a physiological parameter of said person.

ADVANTAGEOUS EFFECT OF THE INVENTION

The invention has the following advantages.

1. The elasticity of the fabric provides sensor position restraint and contact pressure.
2. The elasticity of the fabric additionally provides strain-relief of the wires where they attach to the sensor, and where they exit the apparatus.
3. The porosity of the fabric allows normal heat radiation and moisture evaporation.
4. It is conformal, comfortable, inexpensive, durable, and positioning-repeatable.
5. All hand sizes are accommodated by having 2 or 3 sensor glove sizes available.
6. As added benefits, the look and feel of the present invention are familiar and the setup process quickened, greatly reducing any apprehension by young subjects, as has been witnessed when sensors are being attached.

BRIEF DESCRIPTION OF THE DRAWINGS

FIG. 1 shows a palm-side diagrammatic view of the attachment method used in a clinical study.

FIG. 2 shows a backside diagrammatic view of the attachment method of FIG. 1.

FIGS. 3a–3d are graphical views of actual documentation from the cited clinical study using the methods illustrated in FIGS. 1 and 2, illustrating an instance of anomalous data due to the sensors coming into proximity of a thermal mass.

DETAILED DESCRIPTION OF THE INVENTION

Figure 3B:
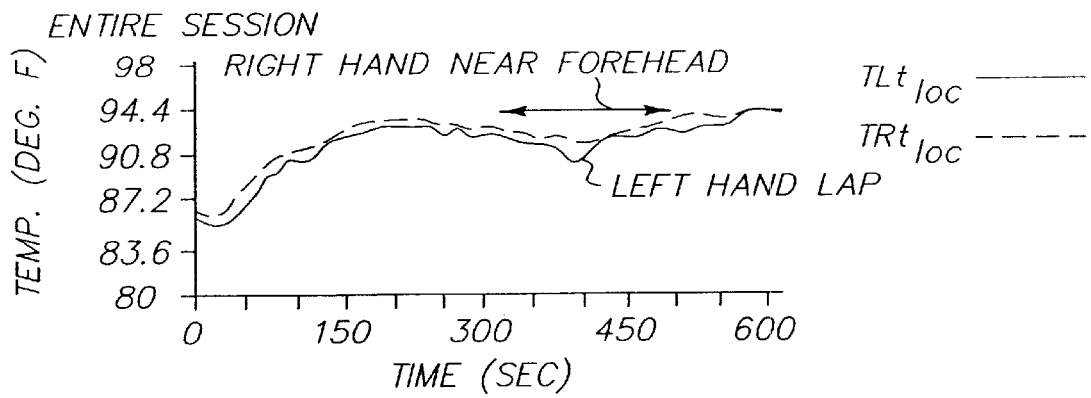
Figure 3C:
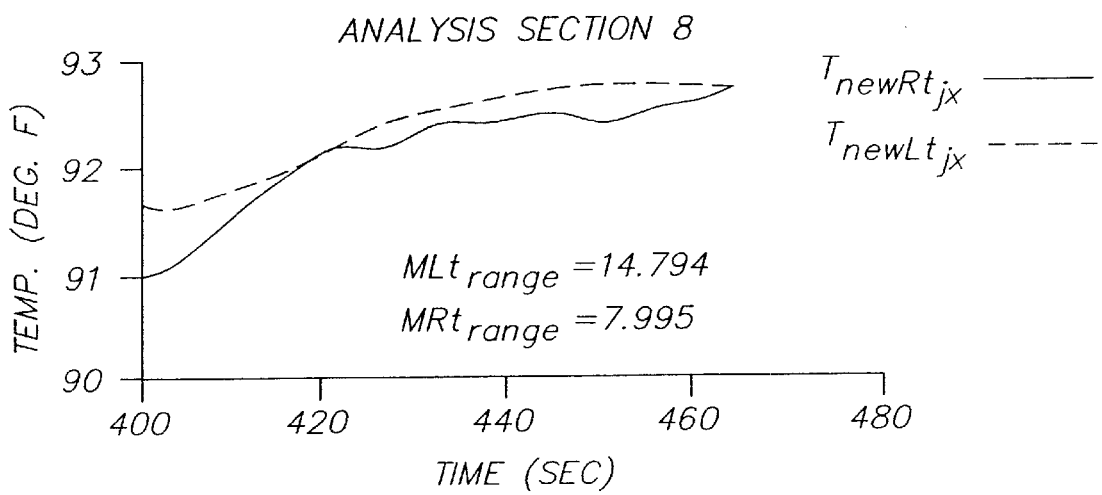
Figure 3D:
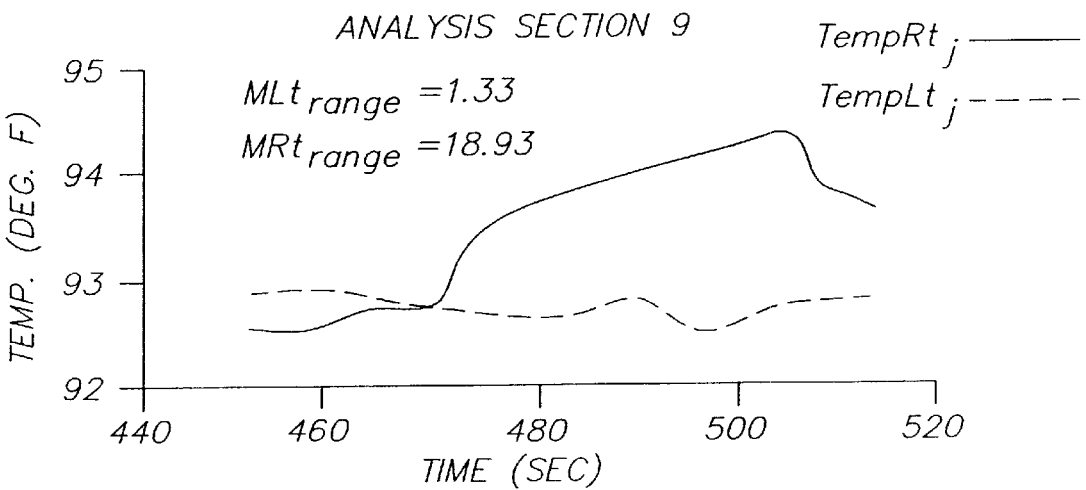

U.S. patent application Ser. No. 09/597,610, filed Jun. 20, 2000, inventors Blazey et al., discloses a technique for determining whether or not an individual has Attention Deficit Hyperactivity Disorder (ADHD). The technique results from the discovery that a signature of ADHD is hidden in fluctuation of peripheral body temperature, such as of the temperature of the skin, as measured at the extremities, such as at a fingertip. Generally, as a person's stress level increases, the blood vessels in the body contract restricting blood flow. This phenomenon is most evident in the body extremities such as the fingers, because the blood vessels in the extremities are small and farthest from the heart. A direct result is a decrease in the peripheral temperature of the extremities.

The inventive technique disclosed in the above patent application requires a protracted thermal sensor measurement of the temperature of a fingertip of the subject. The temperature readings are analyzed to determine whether the subject has ADHD. The temperature can be taken from one or both hands and from one or more fingers on each hand.

In preparation for use during clinical trials of the above technique for determining ADHD, currently-available means for sensor attachment were evaluated. Bands, rings, and tensioned clips, collectively referred to as "cuffs", were rejected for use because they squeeze the finger, becoming uncomfortable over time. The trials sessions duration ranged up to 2 hours.

Also considered was the "clinical-apparatus look" of the means. The subjects ranged in age down to 7 years old, and it was desirable to cause the least apprehension, when possible.

The chosen method was "breathable" tape, which was only partially wrapped around the finger, to prevent the tourniquet effect. It was observed that when the clinician attached the sensors with the tape, there was variability in placement, tightness, and flatness to the skin. Also observed was more-than-slight variance in the integrity of the tape-to-skin bond that allowed both: varying sensor contact pressure, and actual instances of the sensors falling off during a session. This was further aggravated by sweatiness of the fingers.

It was further observed that some subjects, even after having been instructed not to let the sensors touch anything, would tend to rest their hands downward in their lap, on their legs, against their head, or on the armrest of the chair.

The problem with this happening is that, as the sensor gets closer to a thermal mass, such as the subject's body or the arms of the chair, these masses will moderate the small temperature variations to be measured, acting more and more as a very low-pass filter, eventually swamping the finger temperature, as the sensor approaches contact.

It was additionally found that none of the approaches provide any appreciable strain relief for the delicate wires of the sensor. The method used in the clinical trials, illustrated in FIGS. 1 and 2, did mitigate flexure damage to the wires, but only at the sensor.

Referring to FIG. 1, a palm-side view of a hand 1 has a sensor 2 placed against a finger, that is retained in position by a piece of tape 3, with the delicate wires 4 from the sensor routed around the finger. Referring to FIG. 2, a back-side view of the same hand 1 with the partially wrapped sensor tape 3. Also shown is a second piece of tape 5 in place, leaving slack at 6 in the wires 4 to the sensor. Although this provides strain relief for those wires at the sensor during hand and finger movement, it can be realized that this approach does not strain-relieve the wires where they exit 7 this second piece of tape 5. It was observed that the weight of the portion of the wire lead 8 connecting between this tape exit point 7 and the recording equipment (not shown), caused a bend/kink in the wire at the tape exit point 7. This condition was deemed "just acceptable", because there was variability in where this occurred along the wire from session to session, essentially spreading-out the wear, and because we had replacements on hand for the inevitable failures that occurred.

Figure 4A:
FIGS. 4a–4c are graphical views of actual documentation from the clinical study using the methods illustrated in FIGS. 1 and 2, illustrating an instance of anomalous data due to the sensor detaching from it's mount on the participant's finger.
Figure 4B:
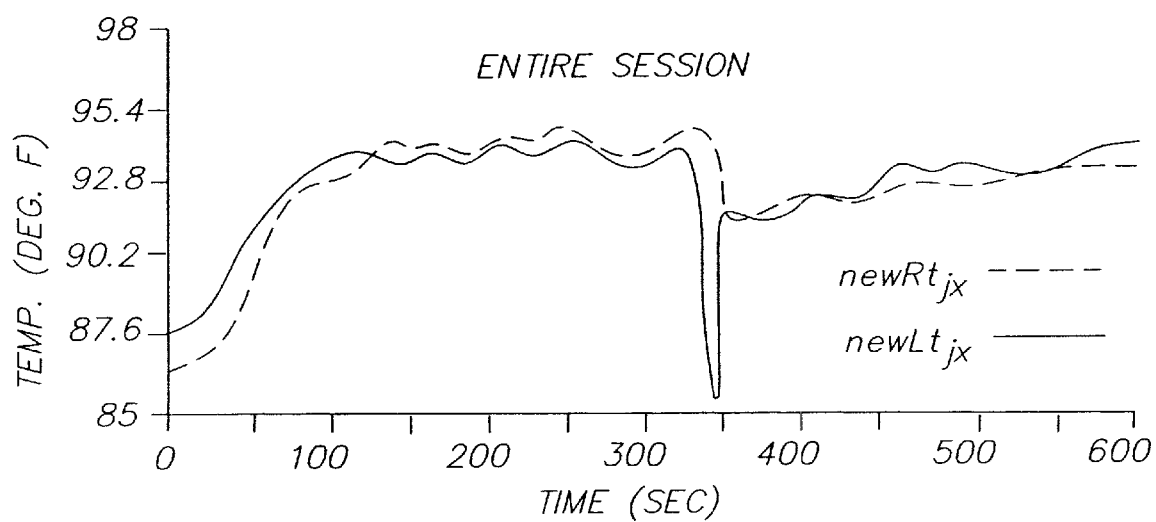
Figure 4C:
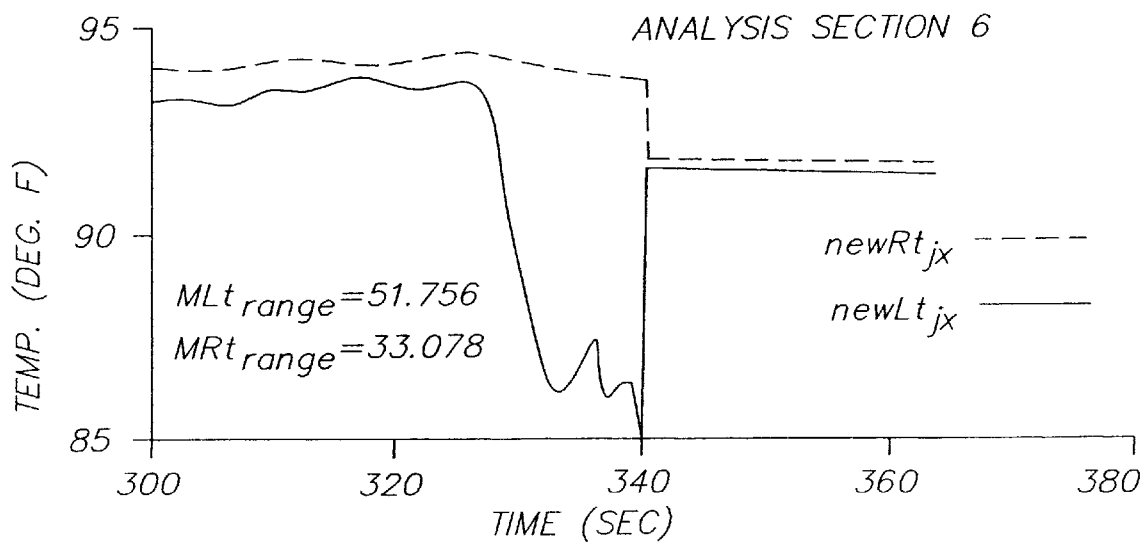

FIGS. 3a–3d and 4a–4c are examples of the sensor problems encountered. In FIGS. 3a and 4a can be seen an imaged excerpt from the respective session logs where the clinician has noted anomalies during the session which correlate with unexpected temperature readings, as evidenced in the raw data plotted in the FIGS. 3b–3d, 4b and 4c. These errant data resulted in anomalous analytical results, that is: high values for the numbers annotated within the lower graphs, FIGS. 3c, 3d and 4c. Because of these and other problems cited herein, all the data had to be manually charted and scrutinized, in reference to the session activity logs. Determinations were made by consensus, and errant data excised, prior to input to the analysis.

In addition, the analysis algorithms then had to be re-coded to be able to handle these gaps in the data.

These problems, therefore, resulted in significantly higher costs, to generate accurate statistical results from the clinical trials. These problems are solved by means of the present invention.

The present invention is a construction resembling a glove, which contains the sensor(s) and wires pre-mounted in their proper positions, to be placed on the hand of a subject during a session that measures any physiological parameter at the extremities of the body. The elasticity of the glove material is designed to provide sufficient position restraint and sensor contact pressure, without acting as a tourniquet, by virtue of the fact that the sensor constraint forces are distributed along the length of the finger, allowing low constriction at any given point.

Conversely, the strain-relief provided to the exiting wires by the present invention is distributed across the entire portion of its fabric over the back of the hand, allowing low restriction at any given point.

The fabric of the present invention is essentially a woven pattern of loops of yarn or like material, roughly resembling that used in scarves, mufflers, pull-over hats, and cold-weather gloves, that is resiliently stretchy, even though the yarn is not. Note that this is possible because the springy loops can deform from their static round shape, to ovals.

Another advantage of the present invention, is that the loops of the material can be made stiff enough to maintain adequate distance between the sensor and any thermal mass that the hand rests against.

This approach also provides the porosity needed for the skin to breathe normally, radiating heat and moisture (confounding factors when not allowed to normally function).

Figure 10:
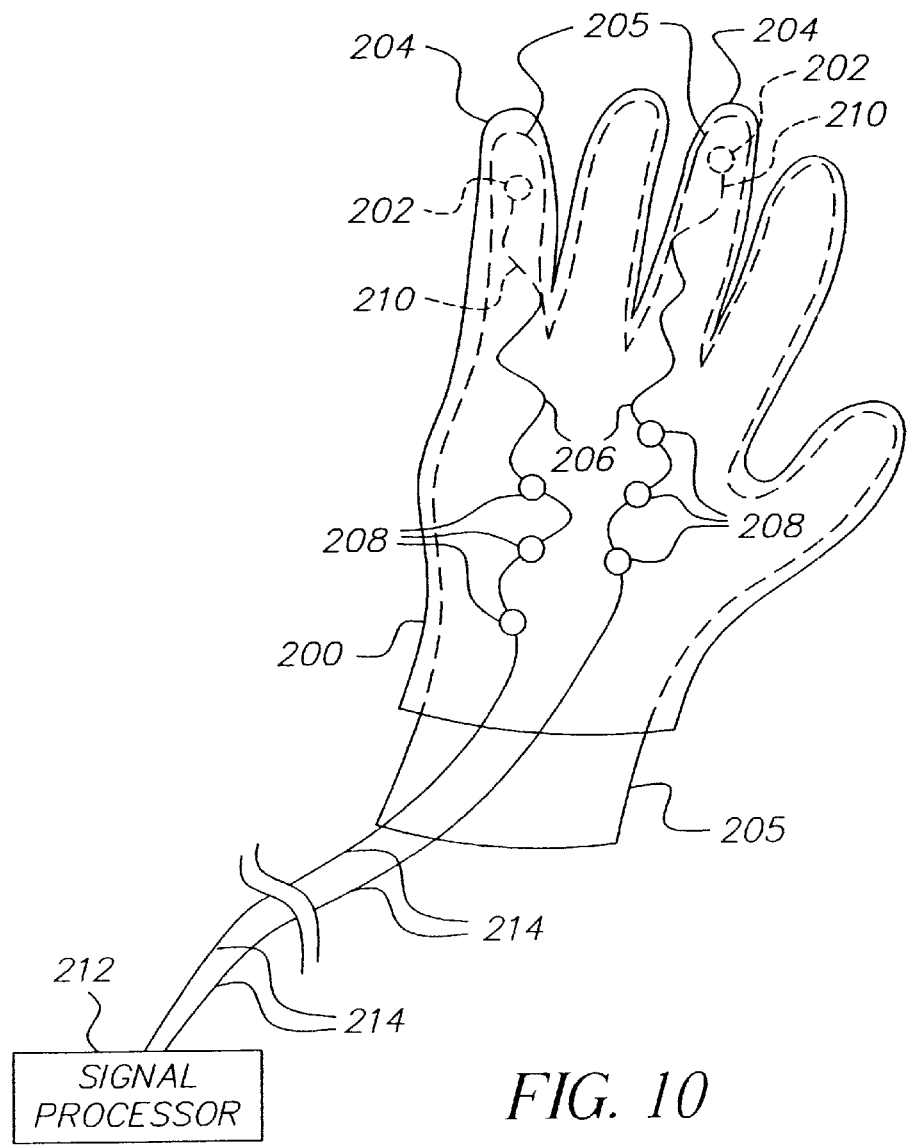
FIG. 10 is an illustration of the present invention, in a preferred embodiment.

Referring now to FIG. 10, there is shown a glove-like embodiment of the present invention. As shown, the apparatus of the present invention 200 is configured to fit on a human subject's hand 205. The apparatus 200 is made of fabric of a woven pattern of loops of yarn or the like material. A sensor 202 is attached to the apparatus 200 at the end of one of its' fingers' 204 so as to be restrained in position against the subject's skin 205 within the apparatus 200. This sensor can be any of known types to sense physiological parameters of the subject, such as a thermal sensor to sense the peripheral skin temperature of the apparatus 200 wearer. An electrical conductor 210 exits the sensor 202 and first wraps around the finger 205 to the back of the hand, continuing in a serpentine fashion 206, threaded through the apparatus 200 fabric, with multiple attachments 208 to the fabric. The signals from sensor 202 are conveyed to signal processor 212 after exit from the present invention, over interconnection 214 (e.g., a wired channel, r.f. wireless channel, infrared optical channel). A second sensor 202 on another finger 204 can also be provided. Thus it will be understood that locating sensor 202 anywhere on apparatus 200, and having more than one sensor 202, e.g., two or more sensors restrained against the skin at different locations, are also within the scope of the invention.

Figure 7:
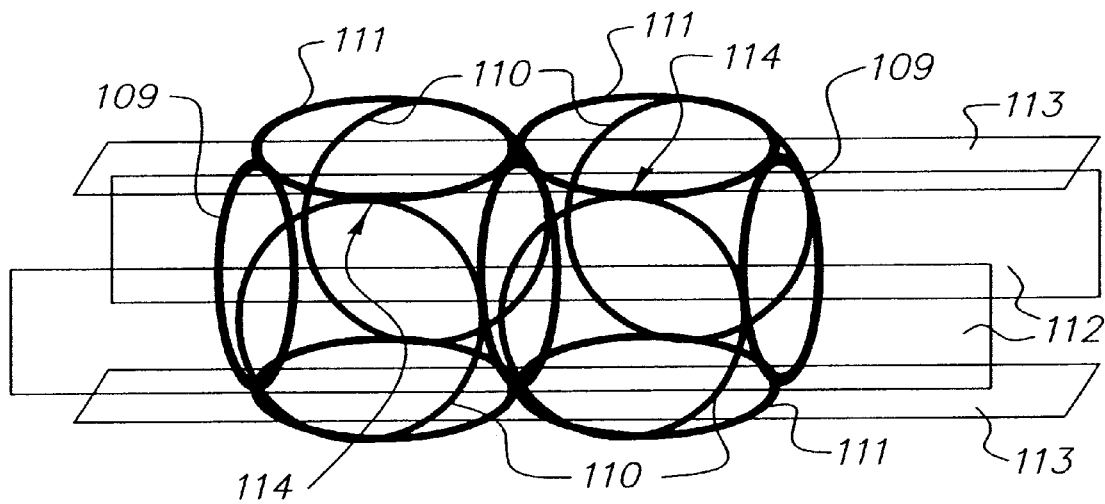
FIGS. 7, 8 and 9 are illustrations of woven patterns useful in the present invention.
Figure 8:
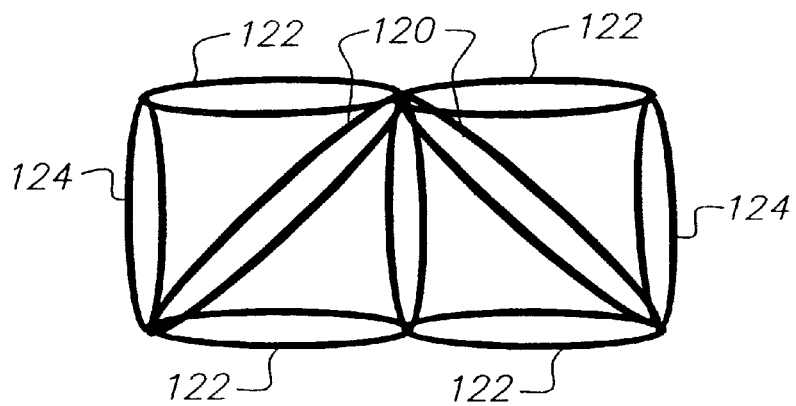
Figure 9:
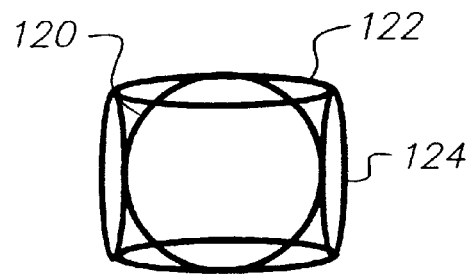

Referring now to FIGS. 7–9, there are shown exemplary configurations of yarn fabric useful in the apparatus of the present invention. FIG. 7 shows one configuration of fabric where loops 109, 110, 111 are arranged continuously to form rows located in stacked planes. Loops 109 are vertically disposed extending perpendicular to the paper, loops 110 are vertically disposed extending parallel to the paper, and loops 111 are horizontally disposed extending perpendicular to the paper. Loops 110 form parallel planes 112 and loops 111 form parallel planes 113 with interconnections 114. This results in a resilient three dimensional cube-like structure being formed. Repeats to the basic structural unit can continue in any direction.

FIG. 8 is a similar configuration of fabric loops employing diagonal loops 120 interconnected with horizontal loops 122 and vertical loops 124. FIG. 9 shows one section of FIG. 8 rotated 90°.

Combinations of these configurations can preferentially allow different amounts and vectors of elasticity throughout the fabric to provide area-specific adjustments, during the design of the apparatus, of the tension of the material as needed for optimal performance. Thus, it is understood, that many such geometrical combinations of loops can be used to best produce the intended attributes of the present invention.

Figure 5:
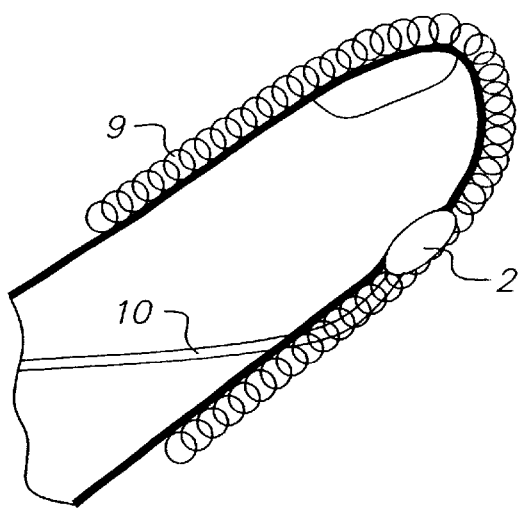
FIG. 5 is a cut-away view of the finger portion of one embodiment of the present invention.

FIG. 5 is a cut-away view of the finger portion of one embodiment of the present invention, showing the woven loops 9 of the present invention's fabric, the mounting location of the sensor 2, and the routing of the wires 10 within the fabric.

Figure 6:
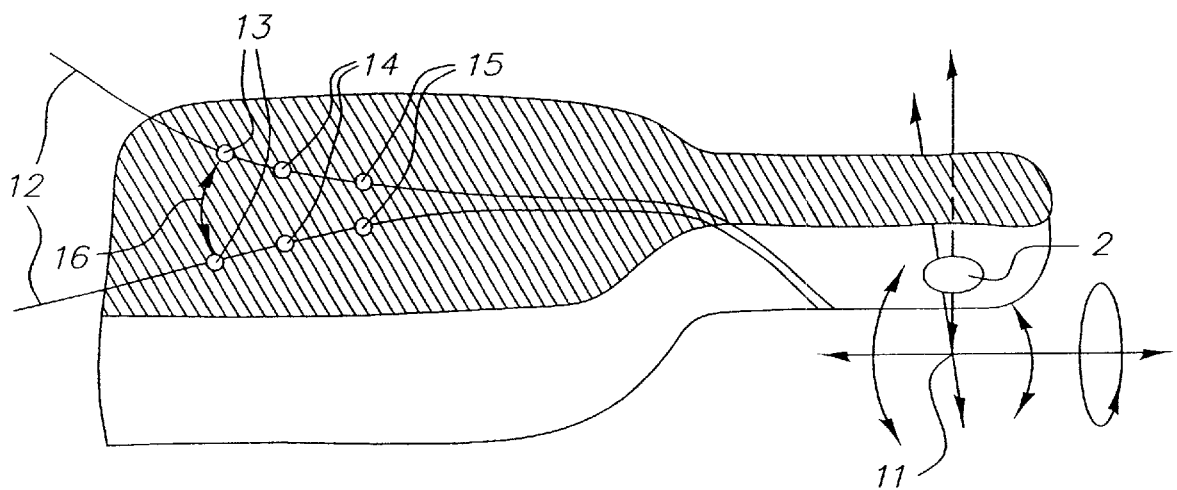
FIG. 6 is a schematic representation of the attributes of the present invention, in a preferred embodiment.

Referring to FIG. 6, the preferred embodiment is shown in a simplified schematic representation, to illustrate the favorable characteristics imparted by the present invention. The elasticity of the present invention's fabric, as a function of the resistance to deformation of the material's loops, is indicated in the form of across-axis arcs 11 where:

a). for the sensor 2, position 'Restraint' occurs, for all axes, in relation to the finger, and b). for the exiting wire lead 12, shown in two possible positions, some "Freedom" of movement 16 occurs, providing a strain-relieving function.

For the case of the latter, additional points are shown where the wire is anchored to the fabric, each point 13, 14, and 15 shown in 2 extended positions representing a hypothetical pull on the wire in 2 opposite directions from its centered rest state: towards the viewer and away from the viewer, in this illustration's perspective. It can be seen that, with the elasticity indicated, this strain-relieving would function equally well if the wire were pulled upward, away from the hand.

Figure 11:
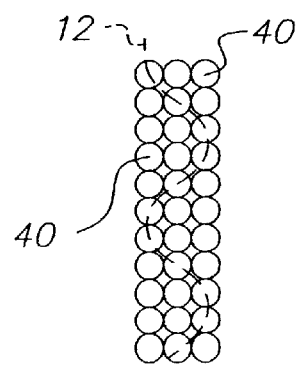
FIG. 11 is an illustration of sensor conductors weaving through the fabric of the present invention, in a preferred embodiment.

The only other possible direction of stress during use is if the wire were pulled towards the wearer's forearm. Strain relief for this case, and during placement and removal of the present invention from the subject's hand, is provided by having the wires 12 route through the loops 40 of the fabric of the present invention in a serpentine fashion (as shown in FIG. 11, and 206 of FIG. 10).

It is therefore shown that the present invention facilitates repeatable and secure sensor attachment, while greatly mitigating flexure damage of sensor wire leads.

Although a sensor for sensing peripheral skin temperature has been described herein used in the present invention, sensors for sensing other physiological parameters can also be used either alone or in combination. Thus, heart rate, heart rate variability, muscle tension measured via surface electromyography (EMG), galvanic skin response (EDR), blood oxygen ($S_pO_2$), peripheral blood flow measured via photoplethysmography (PPG), can also be sensed by appropriate sensors. Moreover, sensors for sensing more than one physiological parameter can also be provided.

Although the present invention has been described using a five-fingered glove, other fabric structures configured to be positioned on an extremity such as a hand or a foot can also be used. Thus, gloves having less than five fingers can be used, as can sock like configurations where a person's hands are unavailable. The thickness of the fabric, the size of the loops, the fabric material will depend on the application and the present invention is not limited thereby.

The invention has been described in detail with particular reference to certain preferred embodiments thereof, but it will be understood that variations and modifications can be effected within the spirit and scope of the invention.

| PARTS LIST | |
|---|---|
| 1 | hand |
| 2 | sensor |
| 3 | sensor tape |
| 4 | wires |
| 5 | sensor tape |
| 6 | wire slack |
| 7 | tape exit point |
| 8 | wire lead |
| 109 | vertical loop |
| 110 | vertical loop |
| 111 | vertical loop |
| 112 | parallel plane |
| 113 | parallel plane |
| 114 | interconnections |
| 120 | diagonal loop |
| 122 | horizontal loop |
| 124 | horizontal loop |
| 200 | glove-like apparatus |
| 202 | sensor |

-continued

PARTS LIST

| | |
|---|---|
| 204 | apparatus 'fingers' |
| 205 | human |
| 206 | conductor |
| 208 | attachment points |
| 210 | wire wrap-around portion |
| 212 | signal processor |
| 214 | signal conveyance channel |

What is claimed is:

1. Apparatus for temporarily attaching a sensor of a physiological parameter to an extremity of a person comprising:
   a fabric structure configured to be positioned on an extremity of a person, said fabric structure formed of loops of yarn like material which exhibit porosity and elasticity; and
   a sensor of a physiological parameter mounted on said fabric structure such that when said structure is positioned on the extremity of a person, said sensor senses a physiological parameter of said person.

2. The apparatus of claim 1 wherein said fabric structure is configured in the shape of a glove having at least one finger to be positioned on the hand of a person.

3. The apparatus of claim 1 wherein said fabric structure is configured by the materials' woven geometries to provide preferential, selective amounts and vectors of elasticity at specific locations of said fabric.

4. The apparatus of claim 2 wherein said sensor is mounted on said at least one finger of said apparatus for sensing a physiological parameter of a person.

5. The apparatus of claim 1 wherein said sensor senses peripheral skin temperature.

6. The apparatus of claim 1 wherein said sensor senses any physiological parameter at a body extremity, that is desired and possible.

7. The apparatus of claim 1 wherein said at least two sensors are mounted on said fabric structure.

8. The apparatus of claim 7 wherein said at least two sensors sense the same physiological parameter.

9. The apparatus of claim 7 wherein said at least two sensors sense at least two different physiological parameters.

10. The apparatus of claim 1 including a conductor attached to said sensor and threaded through said fabric structure formed of loops of yarn, said loops of yarn providing strain relief to said conductor.

11. The apparatus of claim 10 wherein said conductor is threaded through said fabric structure in a serpentine fashion to provide strain relief during placement, use, and removal of the fabric structure on a person's extremity.

12. The apparatus of claim 1 wherein said fabric structure exhibits sufficient porosity to allow normal body heat radiation and moisture evaporation.

13. The apparatus of claim 1 wherein said fabric structure has a thickness, that prevents contact or near contact with other thermal masses.

14. The apparatus of claim 1 wherein said apparatus has the look and feel of a glove for the advantageous effect of reducing apprehension as caused by the 'clinical' appearance of current methods and apparatus.

* * * * *